United States Patent
Vaynberg et al.

(12) 
(10) Patent No.: US 7,110,825 B2
(45) Date of Patent: Sep. 19, 2006

(54) METHOD, A SYSTEM, AND A DEVICE FOR DETECTING AND FOR REDUCING ENERGY LEAKAGE FROM AN ENERGY TREATMENT DEVICES

(75) Inventors: Boris Vaynberg, Zichron Ya'akov (IL); Yotam Zimmerman, Hadera (IL); Yoni Iger, Haifa (IL); Gal Aharonowitz, Gan-Haim (IL)

(73) Assignee: Lumenis Ltd., Yokneam (IL)

( * ) Notice: Subject to any disclaimer, the term of this patent is extended or adjusted under 35 U.S.C. 154(b) by 177 days.

(21) Appl. No.: 10/377,099

(22) Filed: Mar. 3, 2003

(65) Prior Publication Data
US 2004/0176825 A1    Sep. 9, 2004

(51) Int. Cl.
*A61N 1/32* (2006.01)
(52) U.S. Cl. ...................................................... 607/63
(58) Field of Classification Search ............... 604/6.08, 604/41; 607/63, 64, 88, 101; 501/39; 359/595; 700/19
See application file for complete search history.

(56) References Cited

U.S. PATENT DOCUMENTS

| | | | | |
|---|---|---|---|---|
| 3,744,029 A * | 7/1973 | Nyman | .......................... | 700/19 |
| 4,053,210 A * | 10/1977 | Michaelis | .................... | 359/595 |
| 5,977,000 A * | 11/1999 | Sato et al. | ..................... | 501/39 |
| 6,113,566 A * | 9/2000 | Schleicher | ................. | 604/6.08 |
| 7,006,874 B1 * | 2/2006 | Knowlton et al. | ........... | 607/101 |
| 2002/0156471 A1 * | 10/2002 | Stern et al. | .................... | 606/41 |
| 2004/0176823 A1 * | 9/2004 | Island et al. | ................... | 607/88 |

* cited by examiner

*Primary Examiner*—George Manuel
(74) *Attorney, Agent, or Firm*—Pearl Cohen Zedek Latzer, LLP

(57) ABSTRACT

A method, a system and a device for reducing energy leakage from an energy treatment device or system include at least one energy source, at least one sensor to detect energy associated with the at least one energy source or with ambient energy outside the energy treatment device, and a controller to enable a therapeutic energy source upon receiving a signal from the sensor indicating sufficient contact between the energy treatment device and a surface to be treated by the energy treatment device, such that a probability of energy leakage from the device during treatment may be reduced.

12 Claims, 6 Drawing Sheets

METHOD, A SYSTEM, AND A DEVICE FOR DETECTING AND FOR REDUCING ENERGY LEAKAGE FROM AN ENERGY TREATMENT DEVICES

FIELD OF THE INVENTION

The present invention relates in general to energy based medical and aesthetic devices. More particularly, the present invention relates to a method, a system and a device for detecting and for reducing energy leakage, and risk of non-desired damage associated with energy treatment devices or systems.

BACKGROUND

Energy based treatment devices, and in particular electromagnetic based devices for the treatment of medical and aesthetic conditions are gaining popularity among both consumers and practitioners. Current energy based devices utilize a variety of energy forms, such as light including laser energy and Intense Pulsed Light (IPL™), or microwave, and in a variety of wavelengths, and of modalities. One hazard associated with the operation of energy based devices is the possibility of energy leakage, and the accidental exposure of tissue and organs to electromagnetic energy. For example, exposure of the eyes to intense electromagnetic energy may cause transient or even permanent damage to the eyes.

It is therefore desirable to provide a safety arrangement for energy treatment devices that may prevent or at least reduce undesired leakage of energy, and may reduce the possibility of exposure of tissues or areas which are not the subject of treatment.

SUMMARY OF THE INVENTION

Some embodiments of the present invention relate to a method, a system and a device for reducing energy leakage from an energy treatment device or system. Some embodiments of the device for reducing energy leakage from an energy treatment device of the present invention, may include at least one energy source, at least one sensor to detect an energy signature associated with the at least one energy source, and a controller to enable a therapeutic mode of the energy source upon receiving a signal from the sensor indicating sufficient contact between the energy treatment device and a surface to be treated by the energy treatment device, such that a probability of energy leakage from the device during treatment is reduced.

According to further embodiments of the present invention, the controller may be adapted to disable the therapeutic mode of the energy source upon receiving a signal from the sensor indicating insufficient contact between the energy treatment device and a surface to be treated by the energy treatment device.

As part of some embodiments of the present invention, the device for reducing energy leakage from an energy treatment device or system may include an energy source to produce therapeutic energy to be delivered to the treatment area. However, as part of further embodiments of the present invention, the device for reducing energy leakage from an energy treatment device or system may be retrofitted into an energy treatment system according to the prior art.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following non limiting detailed description when read with the accompanied drawings in which:

Figure 1:
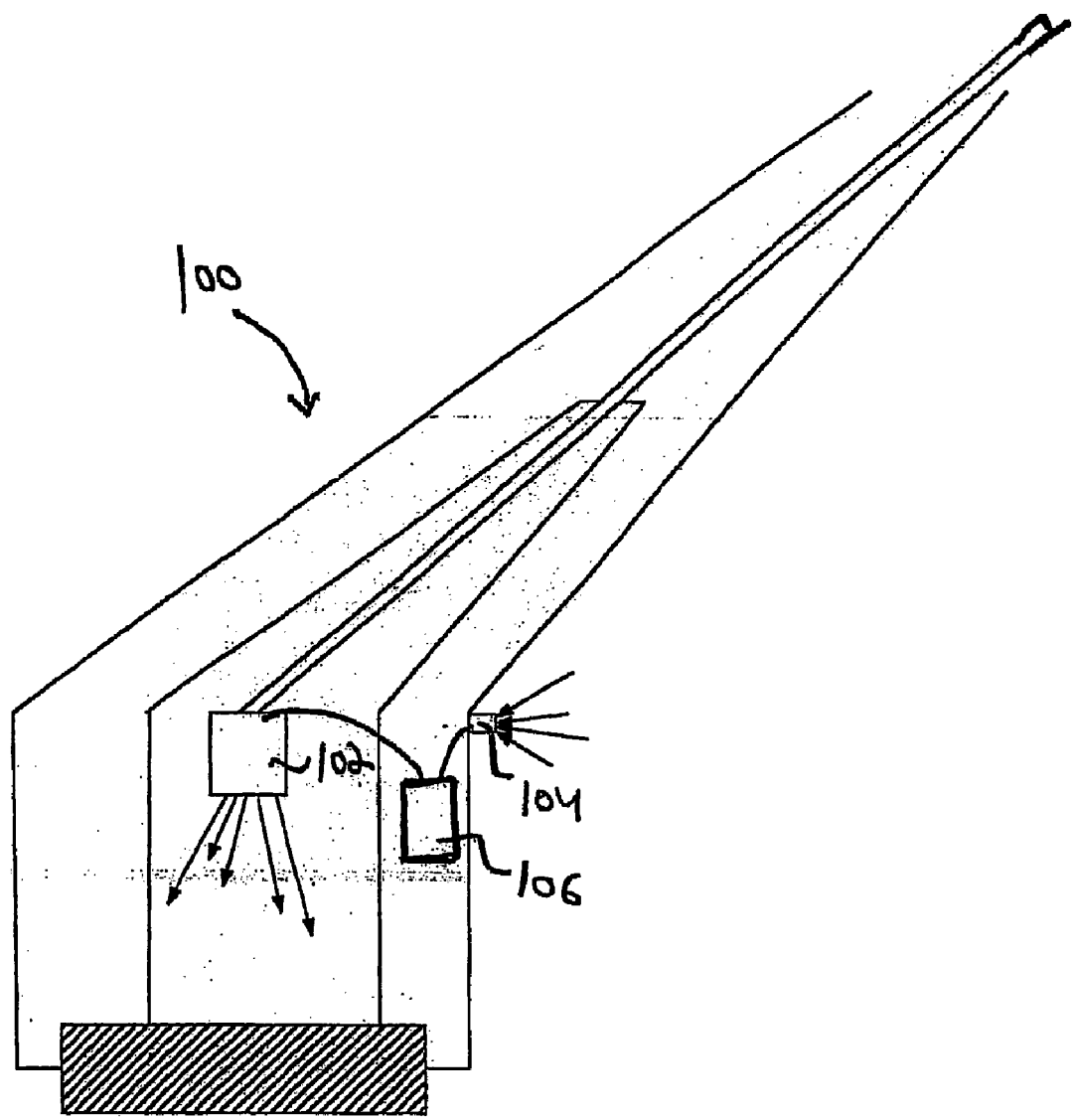
FIG. 1 is a block diagram illustration of an arrangement for reducing energy leakage from an energy treatment device, according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods and procedures have not been described in detail so as not to obscure the present invention.

Although the scope of the present invention is not limited in this respect, for the sake of clarity, throughout the specification and the claims, the term "therapuetic" and similar terms may be used to mean that which may be used to improve or to cure a disease or a disorder, or to remove a non desired element or to treat any medical conditions and any aesthethic conditions.

Although the scope of the present invention is not limited in this respect, for the sake of clarity, some embodiments of the present invention may be used with energy treatment devices for aesthetic treatments (such as hair removal, for example) or for medical treatments. Other embodiments of the present invention may be used with various energy treatment devices utilizing electromagnetic energy. However, it would be obvious to those of ordinary skill in the art how to modify some embodiments of these methods, systems and devices described hereinbelow to use the present invention in conjunction with current or yet to be devised energy treatment devices that may be capable of utilizing other forms of energy to perform a variety of procedures in additional fields.

Although the scope of the present invention is not limited in this respect, for the sake of clarity, some embodiments of the present invention may relate to a device, a system and a method of reducing energy leakage from an energy treatment device or system. It should be noted that the term "leakage reduction" may not be limited to the reduction of the leakage of energy and may include the total prevention of leakage from the energy treatment device or system. Further, it should be noted that the reduction of leakage may also include the reduction of the refraction of light or any other therapeutic energy from the surface of the treated area.

Throughout the specification and the claims, the term "sufficient contact" may be used to mean a level of contact, including but not limited to full-contact, that may be sufficient to reduce the probability of, undesired leakage of energy, or the prevention of such leakage altogether, and consequently reduce the risk of exposure of tissues which are not the subject of treatment to substantial doses of energy. Similarly, the term "insufficient contact" may be used to mean a level of contact that is insufficient to reduce the probability of such undesired leakage of energy. The level of contact that may be represented with each of the above terms may vary in accordance with different energy sources, different configurations, operation parameters and operation protocols, and among different implementations of some embodiments of the present invention. The level of contact that may be represented by each of the above terms may also vary in accordance with various rules and regulations, such as safety regulations.

Some embodiments of the present invention relate to a device, a system and a method of reducing energy leakage from an energy treatment device or system. Some embodiments of the device for reducing energy leakage from an energy treatment device of the present invention, may include at least one energy source, at least one sensor to detect an energy signature associated with the at least one energy source or with ambient energy outside the energy treatment device, and a controller to enable a therapeutic mode of the energy source upon receiving a signal from the sensor indicating sufficient contact between the energy treatment device and a surface to be treated by the energy treatment device, such that a probability of energy leakage from the device during treatment is reduced.

Reference is now made to FIG. 1, which is an illustration of an arrangement for reducing energy leakage from an energy treatment device, in accordance with some embodiments of the present invention. The arrangement for reducing energy leakage from an energy treatment device 100 may include at least one energy source 102, at least one sensor 104 and a controller 106. The sensor 104 may be configured to detect an energy signature associated with the at least one energy source 102.

The controller 106 may be adapted to enable a therapeutic mode of the energy source 102 upon receiving a signal from the sensor 104 indicating sufficient contact between the energy treatment device 100 and the surface to be treated by the energy treatment device 100. According to further embodiments of the preset invention, the controller 106 may be adapted to enable a therapeutic mode of the energy source 102 upon an interruption in the receipt of a signal from the sensor 104 indicating insufficient contact between the energy treatment device 100 and the surface to be treated by the energy treatment device 100. It should be noted that the controller 106 may be otherwise configured to enable, to disable or otherwise control the operation of the energy source 102 in response to a variety of other signals from the sensor 104 associated with the existence of sufficient contact between the energy treatment device and the surface to be treated, or the lack of thereof.

The sensor 104 may be configured to detect energy associated with the energy source 102. For example, the sensor 104 may be configured to detect from among the ambient light impinging upon the sensor 104 an energy signature associated with the energy source 102. The sensor 104 may be adapted to produce a signal indicating sufficient contact, when substantially no energy associated with the energy source 102 is detected. The sensor 104 may also be adapted to produce a signal indicating insufficient contact in response to the detection of energy associated with the energy source 102. In some embodiments, the sensor 104 may discontinue a signal indicating insufficient contact when no energy associated with the energy source 102 is detected. The sensor 104 may be configured to produce a signal indicating sufficient contact upon detecting various doses of energy associated with the energy source 102 or the lack of detection of such energy. These doses of energy may correspond with a variety contact levels, in a scale that may vary from no-contact to full-contact, but axe preferably associated with such levels of contact that may be sufficient to reduce the probability of undesired leakage of energy, or the prevention of such leakage altogether. Similarly, The sensor 104 may be configured to produce a signal indicating insufficient contact upon detecting various doses of energy associated with the energy source 102. Energy detection thresholds may be devised and implemented in the configuration of the sensor 104 to correspond with a variety of sufficient or insufficient contact levels, such that upon detecting an amount of energy that is above or below a certain threshold, the sensor 104 may produce a signal indicating sufficient or insufficient contact. It should be noted that the configuration of the sensor 104 may vary with different operation parameters and operation protocols, among different implementations of some embodiments of the present invention, and in accordance with various rules and regulations, such as safety regulations.

The energy source 102 may be adapted to operate in at least a therapeutic mode. In the therapeutic mode, the energy source 102 may be adapted to produce therapeutic energy. The energy source 102 may also be adapted to operate in a contact testing mode an energy output having specific energy characteristics, or a specific energy signature. The sensor 104 may be configured to detect an energy signature associated with the energy signature that may be produced during the contact testing mode of the energy source 102.

One possible difference between the energy output of the energy source 102 during operation in the therapeutic mode and of the energy output of the energy source 102 during operation in the contact testing mode may be the amount of energy or the fluence of the energy produced during each of the modes of operation. For example, while operating in the therapeutic mode, the energy source 102 may be adapted to produce an energy output in a dosage that may be sufficient to affect human tissue, and while operating in the contact testing mode, the energy source 102 may be adapted to produce an energy output in a dosage below a threshold of biological effect.

A second possible difference between the energy output of the energy source 102 during operation in each of the therapeutic mode and the contact testing mode may be the modulation or the phase of the energy. The energy source 102 may be adapted to modulate the energy output of the energy source 102, such that the modulation of the energy output in the therapeutic mode may be different from the modulation of the energy output in the contact testing mode.

According to some embodiments of the present invention, initially the therapeutic mode of the energy source 102 may be disabled and only the contact testing mode of the energy source 102 may be enabled. The energy source 102 may be activated in the contact testing mode either automatically or in response to a request from a user. Other activating configurations may be used. According to one embodiment of the present invention, the controller 106 may be configured to enable the therapeutic mode of the energy source 102 only upon receiving a signal from the sensor 104 indicating sufficient contact between the energy treatment device 100 and the surface to be treated.

According to further embodiments of the present invention the energy source may be activated in the contact testing mode and in the therapeutic mode simultaneously. Accordingly, the energy source 102 may be adapted to produce an energy output associated with the therapeutic mode of the energy source 102, and at the same time, the energy source 102 may be adapted to produce an energy signature that may be associated with the contact testing mode of the energy source 102.

The controller 106 may be configured to disable the therapeutic mode of the energy source 102 in case no signal from the sensor 104 indicating sufficient contact between the energy treatment device 100 and the surface to be treated by the energy treatment device 100 is received. According to further embodiments of the present invention, the controller 106 may be configured to disable the therapeutic mode of the energy source 102 if a signal from the sensor 104 indicating insufficient contact between the energy treatment device 100 and the surface to be treated by the energy treatment device 100 is received. According to yet further embodiments of the present invention, the controller 106 may be configured to disable the therapeutic mode of the energy source 102 in case during a predetermined period of time, no signal from the sensor 104 indicating sufficient contact between the energy treatment device 100 and the surface to be treated by the energy treatment device 100 is received.

The controller 106 may be configured to cause the complete hardware shut down of the device 100 and all of its components in case no signal from the sensor 104 indicating sufficient contact between the energy treatment device 100 and the surface to be treated is received, or in case such a signal is not received during a predetermined period of time. According to further embodiments of the device of the present invention, the controller 106 may be configured to cause the complete hardware shut down of the device 100 and all of its components in case a signal from the sensor 104 indicating insufficient contact between the energy treatment device 100 and the surface to be treated by the energy treatment device 100 is received.

Figure 2:
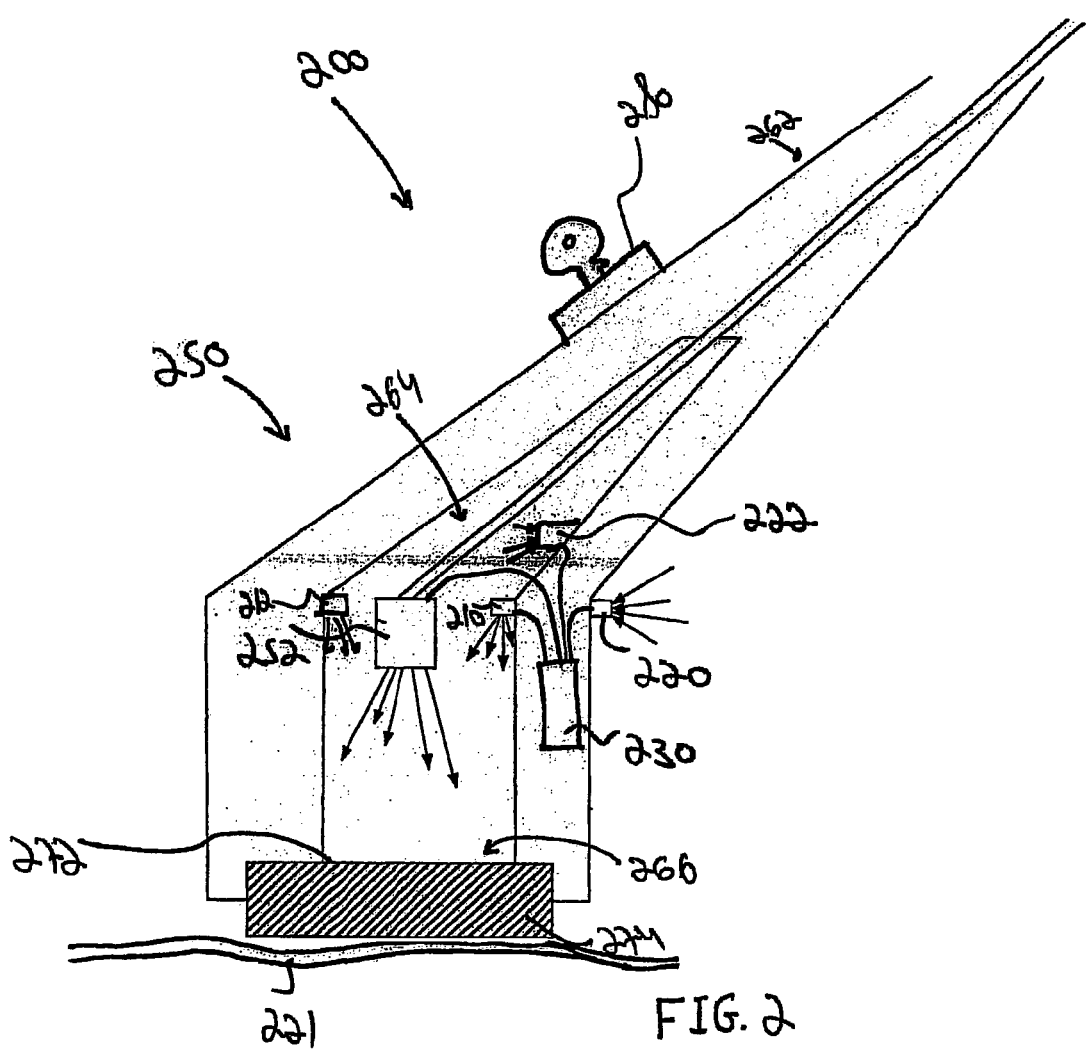
FIG. 2 is a block diagram illustration of an arrangement for reducing energy leakage from an energy treatment device including an ancillary energy source in accordance with some embodiments of the present invention.

Reference is now made to FIG. 2, which is an illustration of an arrangement for reducing energy leakage from an energy treatment device including at least one ancillary energy source, in accordance with some embodiments of the present invention. The arrangement for reducing energy leakage from an energy treatment device 200 may include at least one ancillary energy source 210, at least one sensor 220 and a controller 230.

The controller 230 may be adapted to enable a therapeutic energy source 252 upon receiving a signal from the sensor 220 indicating sufficient contact between the energy treatment device 200 and a surface 221 to be treated. It should be noted that the controller 230 may be otherwise configured to enable, to disable or otherwise control the operation of the ancillary energy source 210 in response to a variety of other signals from the sensor 220 associated with the existence of sufficient contact between the energy treatment device and the surface to be treated, or the lack of thereof.

The sensor 220 may be configured to produce a signal indicating sufficient contact between the energy treatment device 200 and the surface to be treated. The sensor 220 may also be configured to produce a signal indicating insufficient contact between the energy treatment device 200 and the surface to be treated. The sensor 220 may be configured to produce a signal indicating sufficient contact upon detecting various doses of energy associated with the ancillary energy source 210 or the lack of detection of such energy. These doses of energy may correspond with a variety contact levels, but are preferably associated with such levels of contact that may be sufficient to reduce the probability of undesired leakage of energy, or the prevention of such leakage altogether, including but not limited to full-contact. Similarly, The sensor 220 may be configured to produce a signal indicating insufficient contact upon detecting various doses of energy associated with the energy source 210.

In the embodiment shown, the arrangement for reducing energy leakage from an energy treatment device 200 is implemented in conjunction with a typical energy treatment device. The energy treatment device 200 may include a treatment accessory 250 and a therapeutic energy source 252. The treatment accessory 250 may include one or more of the following: a handpiece, an articulated arm with or without optical fiber and a variety of other accessories.

In the embodiments shown in FIG. 2, the treatment accessory 250 may be a handpiece. The handpiece 250 may include a handle portion 262, an inner portion 264, such as an inner cavity, and an output portion 266. The ancillary energy source 210 and the therapeutic energy source 252 may be positioned within the inner portion 264 of the handpiece 250. The sensor 220 may be positioned outside the handpiece 250. The output portion 266 may allow the transfer of energy from both the ancillary energy source 220 and the therapeutic energy source 252 out of the handpiece 250 through an aperture 272, for example on to the area 221 to be treated.

The therapeutic energy source 252 and/or the ancillary energy source 220 may also be positioned outside the treatment accessory 250, and the energy from therapeutic energy source 252 and/or the ancillary energy source 220 may be carried to a desired location via a wave guide or some other suitable energy guide (not shown). For example, the output end of the wave guide may be positioned within the inner portion 264 of the treatment accessory 250 in a manner to allow the energy from therapeutic energy source 252 and/or the ancillary energy source 220 to pass through the output portion 266 of the treatment accessory 250 onto the area to be treated.

The output portion 266 may further include an optical element 274. The optical element 274 may be fitted into the aperture 272. The optical element 274 may be adapted to guide, couple or transfer energy from the therapeutic energy source 252 to the treatment area. For example, in case the therapeutic energy source 252 is a laser producing electromagnetic energy output, and the energy guide 274 is a sapphire guide, the electromagnetic radiation may propagate through the aperture 272 and through the sapphire guide, to allow the exposure of the area to be treated 221 to the laser energy. It should be noted that the present invention is not limited to light treatment devices but may be used with all energy based devices, in virtually all frequency ranges that are known to have therapeutic value.

The energy treatment device 200 may be used for aesthetic treatments. For example, the energy treatment device 200 may be used for removing hair from a patient's body. The energy treatment device 200 may be used for other aesthetic or medical treatments or procedures and is not limited to any one specific treatment or procedure. Additionally, it should be noted that the scope of the invention is not limited to aesthetic and/or medical treatments or procedures, and that the present invention and any of its elements may be used in a variety of fields for a variety of purposes, including adaptations to currently available devices and systems.

As part of one embodiment of the present invention, the therapeutic energy source 252 may be adapted to produce light. As part of further embodiment of the present invention, the, therapeutic energy source 252 may be a laser such as a laser diode or diode bar, a certain spectrum or an IPL lamp, a LED, a microwave energy source or any other suitable energy source.

The ancillary energy source 210 may be configured to produce an energy output having predetermined characteristics. For example, the ancillary energy source 210 may produce a pulsed energy output having a specific pulse pattern, energy having a specific wavelength or frequency, or energy having a specific oscillation pattern. The sensor 220 may be configured to detect energy having characteristics or components that may be substantially corresponding to the characteristics of the energy produced by the ancillary energy source 210. For example, in case that the ancillary energy source 210 is a monochromatic light source capable of producing light having specific spectra, the sensor 220 may be adapted to detect from among the ambient light impinging upon the sensor 220 the electromagnetic radiation having a wavelength that is within a predefined spectra substantially corresponding to the monochromatic light produced by the ancillary energy source 210. According to further embodiments of the present invention, the ancillary energy source 210 may be adapted to produce a particular modulation of the energy output. The sensor 220 may be configured to detect modulated energy that is substantially corresponding in modulation to the pattern of the modulation of the energy produced by the ancillary energy source 210.

According to further embodiments of the present invention, the ancillary energy source 210 may be a laser, or a light emitting diode (LED) and the sensor 220 may be a photodiode (PD). The LED may be adapted to produce a narrow spectrum light, possibly monochromatic light, modulated light or any combinations thereof. The PD may be capable of detecting from among the ambient light impinging upon the sensor 220, electromagnetic radiation having a wavelength, spectrum or modulation that is within a predefined spectra or pattern of modulation substantially corresponding to the light produced by the ancillary energy source 210. It should be noted however, that the scope of the invention is not limited in this respect, and that other suitable elements may be used.

The ancillary energy source 210 may be coupled with a filter or filters or other energy manipulation elements (not shown). When the ancillary energy source 210 is activated, energy from the ancillary energy source 210 may impinge upon the filter coupled thereto. The filters may allow only a portion of the energy to pass through. Filters may be selected to allow only a selected portion of the energy to pass through, such that the energy exiting the filters may have predetermined characteristics. The sensor 220 may also be coupled with a filter of filters or other energy manipulation elements (not shown). Thus, when ambient energy may impinge upon the filter or filters coupled to the sensor 220, the filter may be selected to allow only a predetermined portion of the energy to pass through, such that the energy passing through the filters onto the sensor 220 may have predetermined characteristics. Suitable filters may be selected to allow the passage of only such energy that is substantially corresponding to the energy exiting the ancillary energy source 210 and passing through any filters that may be coupled to the ancillary energy source 210.

Those with ordinary skill in the art may appreciate that various energy forms in all frequency ranges known to have therapeutic value, under suitable conditions, may react differently when applied to the skin or other tissue. For example, light having a wavelength that is within a certain spectrum range or ranges may have substantially high penetration capabilities through a certain tissue layer or layers, while light in different wavelengths may be have poor penetration through the same tissue layer or layers due to high absorption of such light in such tissue. Consequently, when using certain forms of energy and in certain frequencies, although full contact may exist between the treatment device 200 and the surface to be treated, some of the energy from the ancillary energy source 210 may pass through the skin and/or other tissue, and may be detected by the sensor 220. For example, electromagnetic energy in the red and the near infrared region of the spectrum, is known in the art to have better penetration capabilities through the skin and other tissue in comparison with similar doses of electromagnetic radiation in the blue or green region of the spectrum.

Accordingly, it may be desirable to select an ancillary energy source 210 having an energy output that is characterized in poor skin and other relevant tissue penetration. For example, a blue-green LED capable of generating monochromatic light having a wavelength in the range of 470–530 nm may be used due to the poor skin penetration that is characteristic of blue-green light. Other suitable ancillary energy sources 210 capable of producing other forms of energy in other frequencies may be used, including, but not limited to, an ancillary energy source 210 that may be adapted to produce red or infra-red light. In these and other embodiments of the present invention, the sensor 220 may be configured to generate a signal indicating sufficient contact between the energy treatment device and the surface to be treated, only when the amount of energy associated with the energy produced by the ancillary energy source 210 detected by the sensor 220 is below a predetermined threshold.

As part of some embodiments of the present invention, an energy treatment device 200 may include more than one ancillary energy source 210. Each one of the plurality of ancillary energy sources 210 may provide a backup for the operation of the other ancillary energy sources 210, for example, in case that one of the ancillary energy source is malfunctioning. Thus, the use of more than one ancillary energy sources 210 may increase the likelihood of detection of actual or true energy leakage, and may reduce the probability of detection failure or false detection.

Furthermore, the inclusion of two or more ancillary energy sources 210 capable of producing distinct energy outputs may also reduce the probability of detection failure or false detection. For example, when the energy produced by a first ancillary energy source 210 is affected by the treatment conditions, and as a result the energy is poorly or falsely detected by the sensor 220, the energy produced by a second ancillary energy source 212 may not be affected by the same treatment conditions, and may thus be correctly detected (or correctly not detected) by the same sensor 220 or by a different sensor, thereby increasing the probability of detection of actual or true energy leakage.

According to some embodiments of the present invention, when the energy treatment device 200 is in standby or inactive mode, the therapeutic energy source 252 may be disabled. A request for the activation of the therapeutic energy source 252 (either automatically or user generated) may trigger the activation of the ancillary energy source 210 and of the sensor 220. The therapeutic energy source 220 may be enabled and its activation may be permitted only after the controller 230 had received a signal from the sensor 220 indicating sufficient contact between the energy treatment device 200 and a surface 221 to be treated. The controller 230 may allow the therapeutic energy source 252 to remain activated for a predetermined period of time. The controller 230 may enable the therapeutic energy source 252 again, only after the controller 230 had received a signal from the sensor 220 indicating sufficient contact. The controller 230 may disable the therapeutic energy source 252 at any point during or prior to the activation of the therapeutic energy source 252 upon receiving a signal from the sensor 220 indicating no sufficient contact.

The energy treatment device 200 may further include a second sensor 222 positioned within the inner portion of the treatment accessory 264. The second sensor 222 may be configured to produce a signal indicating that the ancillary energy source or sources 210 are functioning properly. The second sensor 222 may produce the signal indicating that the ancillary energy source or sources 210 are functioning properly upon the detection of energy associated with the ancillary energy source or sources 210. According to some embodiments of the present invention, the second sensor 222 may produce the signal indicating that the ancillary energy source or sources 210 is malfunctioning when not detecting energy associated with the ancillary energy source or sources 210, or when the energy detected does not comply with predefined requirements. The controller 230 may enable the therapeutic energy source 252 only upon receiving a signal from both the first sensor 220 and a signal from the second sensor 222 indicating sufficient contact and proper functionality, respectively.

As part of further embodiments of the present invention, the energy treatment device 200 may further include additional safety promoting arrangements 280 that may be operated in conjunction with the arrangement for reducing energy leakage from an energy treatment device of some embodiments of the present invention. For example, the energy treatment device 200 may include a unique safety key, a number pad associated with a unique password to be punched in, and other similar safety promoting arrangements 280. The therapeutic energy source 252 may be enabled only if all the safety requirements of all the safety arrangements are met. Additional safety arrangements 280 may also be included.

Figure 3:
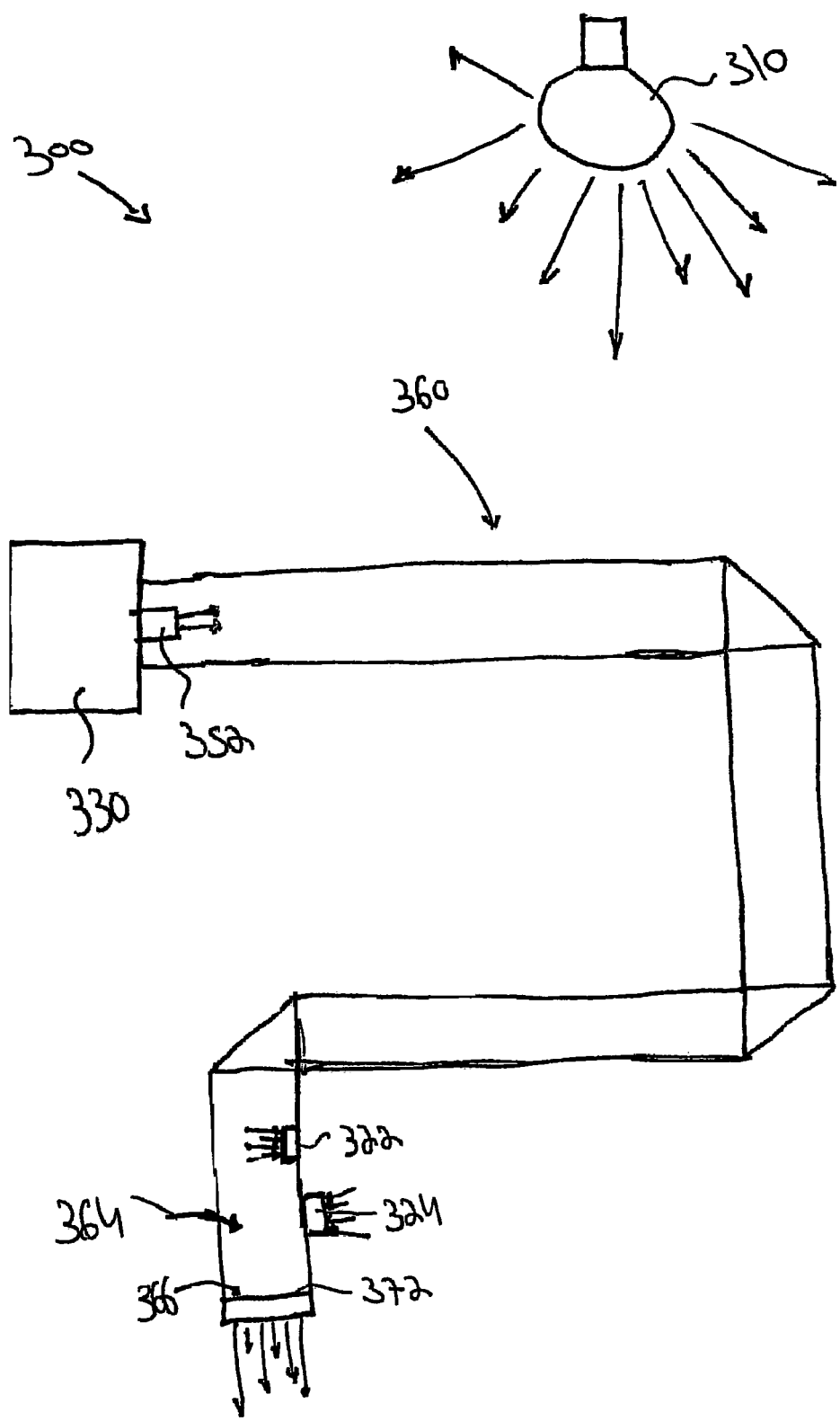
FIG. 3 is a block diagram illustration of an arrangement for reducing energy leakage from an energy treatment device in accordance with further embodiments of the present invention.

Reference is now made to FIG. 3, which is an illustration of an arrangement for reducing energy leakage from an energy treatment device, in accordance with further embodiments of the present invention. The arrangement for reducing energy leakage from an energy treatment device may include at least one ancillary energy source 310, a first sensor 322, a second sensor 324 and a controller 330.

In the embodiment shown, the arrangement for reducing energy leakage from an energy treatment device may be implemented in conjunction with a typical energy treatment device 300. The energy treatment device 300 may include a treatment accessory 360 and a therapeutic energy source 352. The treatment accessory 360 may be an articulated arm.

Other treatment accessories may be used. The articulated arm 360 may include an inner portion 364 and an output portion 366. The first sensor 322 and the therapeutic energy source 352 may be positioned within the inner portion 364 of the articulated arm 360. The ancillary energy source 310 and the second sensor 324 may be located outside the articulated arm 360. The output portion 366 may include an aperture 372. The aperture 372 may permit the passage of energy from the therapeutic energy source 352 out of the articulated arm 360 and also the passage of energy from the ancillary energy source 310 into the inner portion 364 of the articulated arm 360. The device 300 may also include filters (not shown). The filters may be coupled to the ancillary energy source 310 and/or to the sensor 322, as has been described above.

According to some embodiments of the present invention the ancillary energy source 310 may be any one of conventional incandescent light bulbs used to illuminate domestic or office rooms in case the ancillary energy source 310 used is an incandescent light bulb, the output of the ancillary energy source 310 may be the circumfused ambient light illuminating the room.

The controller 330 may be adapted to enable the therapeutic energy source 352 only upon receiving a signal from both the first and the second sensors 322 and 324 indicating sufficient contact. According to further embodiments of the present invention, the first sensor 322 may produce a signal indicating sufficient contact between the energy treatment device 300 and a surface to be treated when substantially no energy associated with the at least one ancillary energy source 310 is detected. The second sensor 324 may produce a signal indicating sufficient contact between the energy treatment device 300 and a surface to be treated when a dose of energy associated with the at least one ancillary energy source 310 that exceeds a predetermined threshold is detected. This and other embodiments of the present invention, may used be to unable the operation of the therapeutic energy source or the therapeutic mode of the energy source under appropriate ambient light conditions.

Figure 4:
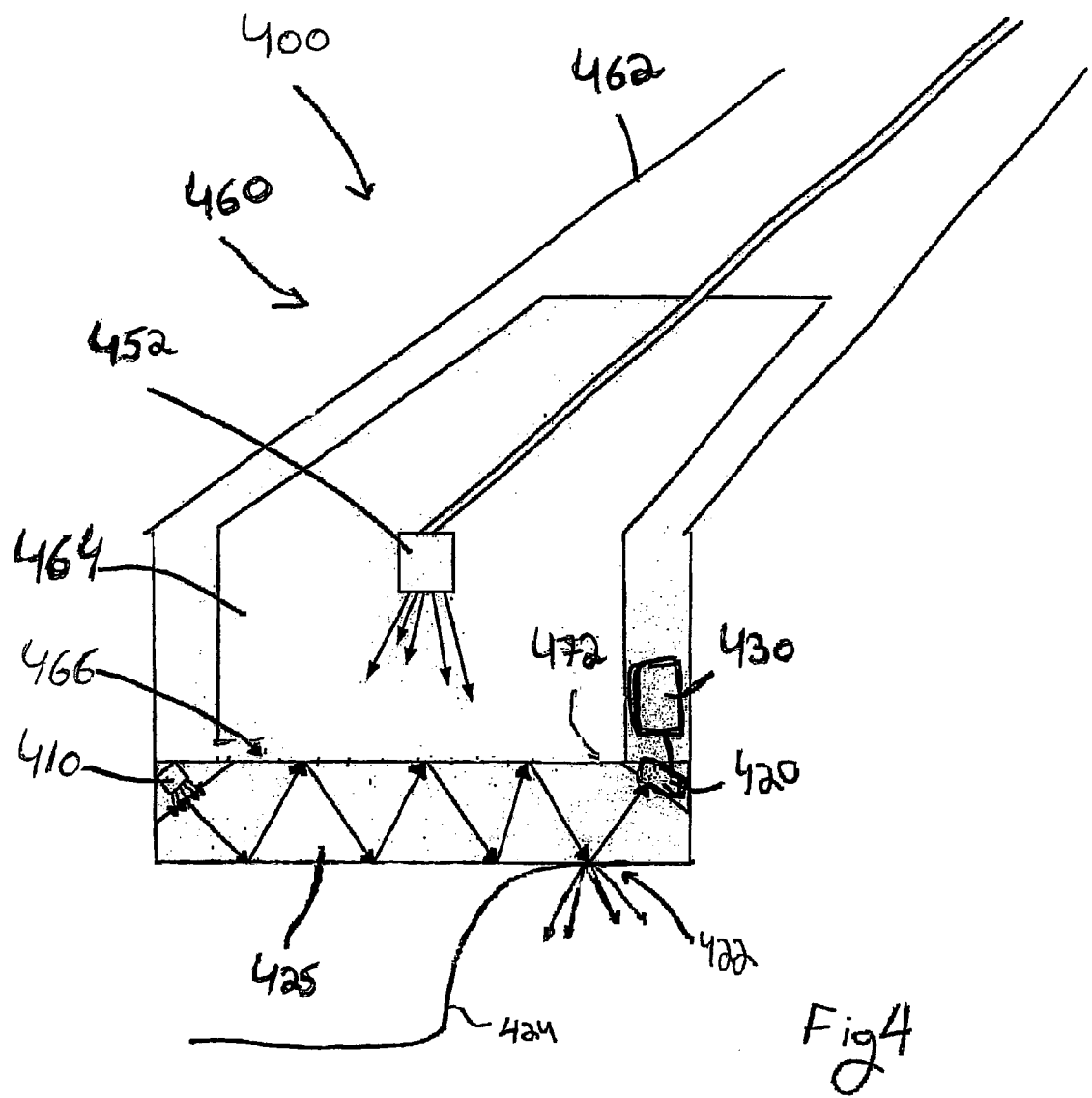
FIG. 4 is a block diagram illustration of an arrangement for reducing energy leakage from an energy treatment device in accordance with yet further embodiments of the present invention.

Reference is made now to FIG. 4, which is an illustration of an arrangement for reducing energy leakage from an energy treatment device in accordance with yet further embodiments of the present invention. The arrangement 400 may include at least one ancillary energy source 410, a sensor 420, a waveguide 425 and a controller 430. The ancillary energy source 410 and the sensor 420 may be coupled to the waveguide 425. The waveguide 425 may be adapted to transmit energy from the ancillary energy source 410 to the sensor 420. According to some embodiments of the present invention, the waveguide 425 may also be adapted to, carry therapeutic energy produced by the therapeutic energy source 452 to an area to be treated.

In the embodiment shown, the arrangement for reducing energy leakage from an energy treatment device is implemented in conjunction with a typical energy treatment device 400. The energy treatment device 400 may include a treatment accessory 460 and a therapeutic energy source 452. The treatment accessory 460 may include a handle portion 462, an inner portion 464 and an output portion 466. The therapeutic energy source 452 may be positioned within the inner portion of the treatment accessory 464. The output portion 466 may include an aperture 472. The aperture 472 may allow the passage of energy from the therapeutic energy source 452 out of the treatment accessory 460 onto the treatment area. The waveguide 425 may be coupled to the treatment accessory 460. The waveguide 425 may be coupled to the output portion 466 of the treatment accessory 460. The waveguide 425 may also allow the passage of energy from the therapeutic energy source 452 out of the treatment accessory 460 onto the treatment area.

The wave guide 425 may be fabricated using any appropriate material or material combination that may be suitable for the particular transmission of energy. Those of ordinary skill in the art may appreciate that the energy may propagate through the wave guide 425 in a series of reflections. The quality of transmission of a specific wave guide may be associated with, among other factors, the surroundings of the waveguide. The refraction index of the material as well as the quality of the environment surrounding the wave guide may affect the reflections of the energy through the waveguide. When optimal transmission conditions are provided, the energy may propagate through the wave guide in a series of reflections with very little or substantially no energy leakage. This condition is commonly referred to as total internal reflections.

The wave guide 425 may be configured to enable the transmission of the energy produced by the ancillary energy source 410 through the wave guide 425 in a series of total internal reflections when surrounded with a first material or environment. In some embodiments of the present invention, the first material or environment may be air. The wave guide 425 may also be configured to enable a leakage of energy through the wave guide walls when surrounded with a second material or environment. In such case, the wave guide 425 may provide a lesser transmission of energy when surrounded with that specific second material or environment. The second material may be tissue or skin tissue.

In the embodiment shown, the portion of the wave guide 425 that is surrounded by air may enable the energy produced by the ancillary energy source 410 to propagate through the wave guide 425 in a series of total internal reflections. The portion of the wave guide 425 that is in contact with the skin 424 at area 422 may allow a leakage of energy produced by the ancillary energy source 410. As a result, the amount of energy that may be carried by the wave guide 425 to the sensor 420 may be substantially lower when the wave guide 425 is in sufficient contact with the area to be treated, when compared with the amount of energy that may be carried by the wave guide 425 to the sensor 420 when the wave guide 425 is surrounded with air.

Those of ordinary skill in the art may appreciate that among other things also the angle of incidence of the energy upon the input aperture of the waveguide 425 may affect the reflectance of the energy through the wave guide 425. Thus, the angle of incidence of the energy produced by the ancillary energy source 410 on the input portion of the wave guide 425 may be selected to enable good internal reflectance of the energy inside the wave guide 425 when surrounded with a specific environment, such as air and the ancillary energy source 410 may be positioned accordingly. The angle of incidence of the energy produced by the ancillary energy source 410 upon the input portion of the waveguide 425 may also be selected to allow controlled leakage of energy when surrounded with a specific environment, such as skin tissue.

According to some embodiments of the present invention, the sensor 420 may be configured to generate a signal indicating sufficient contact between the energy treatment device 400 and a surface to be treated only when the amount of energy detected by the sensor 420 is within a predetermined range. The predetermined range may be associated with the amount of energy that may be carried by the wave guide 420 when surrounded by a specific environment or material.

According to some embodiments of the present invention, when a portion of the wave guide 425 is in contact with the skin, some of the energy carried by the wave guide 425 may be radiated away, in point 422 and the amount of energy that may be transmitted to the sensor 420 may decrease. The predetermined range may be associated with the amount of energy that may be carried by the wave guide 425 to the sensor 420 when the wave guide 425 is in sufficient contact with the area to be treated. The predetermined range may also be associated with the amount of energy that may be transmitted by the wave guide 425 to the sensor 420 when the portion of the wave guide 425 facing the skin is in sufficient contact with the skin.

The device 400 may also include a variable transmission element (not shown). The variable transmission element may be positioned along the path of the therapeutic energy that may be produced by the therapeutic energy source 452. The variable transmission element may include at least two modes of energy transmission, a transmission mode and a blocked mode. When in the transmission mode, the variable transmission element may allow the therapeutic energy to pass through the substantially unaffected the variable element. When in the blocked mode of transmission the variable transmission element may allow only a portion of the therapeutic energy to pass through or may prevent the energy from passing through it altogether. The variable transmission element may include one or more of a group of variable opacity elements such a liquid crystal, a polarized optical element, a mechanical shutter and any other suitable elements that may provide at least two modes of energy transmission as discussed above.

The variable transmission element may be coupled to the output portion of the treatment accessory 466. The default mode of the variable transmission element may be the blocked mode of transmission, such that substantially no therapeutic energy may be transmitted out of the treatment accessory 460. The variable transmission element may switch to the transmission mode at a certain interval after, or upon receiving a signal from the controller 430 indicating substantially sufficient contact between the energy treatment device 400 and a surface to be treated. According to some embodiments of the present invention, the variable transmission element may be combined with some embodiments of the leakage reduction arrangement discussed hereinabove or with any other suitable safety arrangements. It should be noted that the variable transmission element may be used in conjunction with a variety of energy sources capable of producing a variety of energy outputs in a variety of frequencies, including but not limited to, electromagnetic energy.

Figure 5:
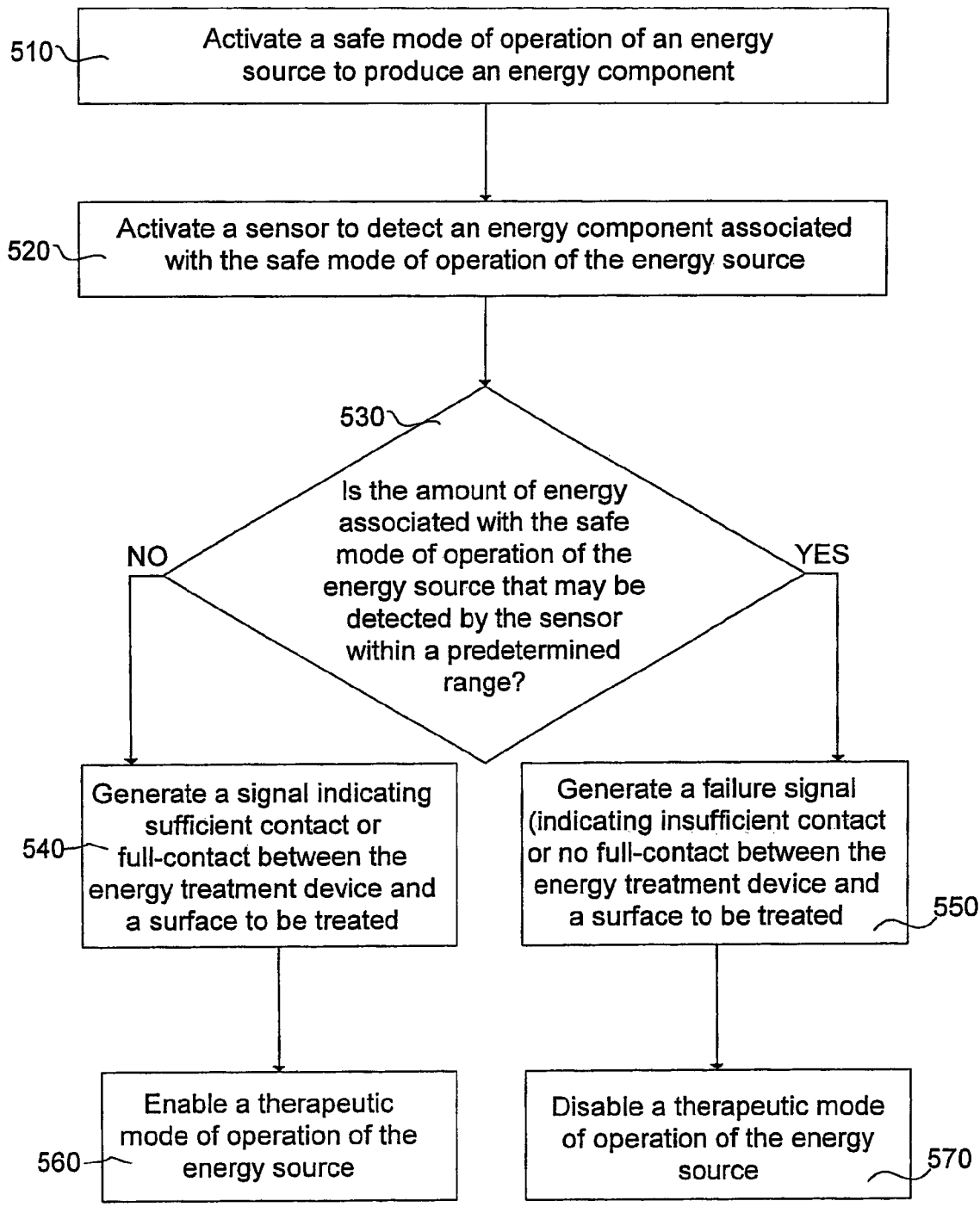
FIG. 5 is a flow chart illustration of a method of reducing energy leakage from an energy treatment device in accordance with some embodiments of the present invention.

Reference is now made to FIG. 5, which is an illustration of a method of reducing energy leakage from an energy treatment device in accordance with some embodiments of the present invention. According to some embodiments of the present invention, the method of reducing energy leakage from an energy treatment device may include activating a safe mode of an energy source to produce an energy component (block 510). For example, the safe mode of an energy source may be activated to produce electromagnetic radiation in a specific modulation. According to some embodiments of the present invention, the safe mode of an energy source may be activated to produce an energy component having predetermined characteristics.

According to some embodiments of the present invention, the method of reducing energy leakage from an energy treatment device may include activating a sensor to detect an energy component associated with the safe mode of the energy source (520). The amount of energy associated with the safe mode of the energy source that may be detected by the sensor may be calculated to determine, whether the amount of energy associated with the safe mode of the energy source that may be detected by the sensor, is within a predetermined range (block 530). If the amount of energy associated with the safe mode of the energy source that may be detected by the sensor is outside the predetermined range, the sensor may generate a signal indicating sufficient contact between the energy treatment device and a surface to be treated (block 540). Upon receiving a signal from the sensor indicating sufficient contact between an energy treatment device and a surface to be treated by the energy treatment device, a therapeutic mode of the energy source may be enable (block 560).

However, if the amount of energy associated with the safe mode of the energy source that may be detected by the sensor is within a predetermined range the sensor may generate a failure signal (block 550). The failure signal may indicate insufficient contact between the energy treatment device and the surface to be treated. Upon receiving a signal from the sensor indicating insufficient contact between an energy treatment device and a surface to be treated, a therapeutic mode of the energy source may be disabled (block 570). The signal from the sensor indicating insufficient contact between an energy treatment device and a surface to be treated by the energy treatment device may also be transmitted to an indicator, such as an LED display.

According to some embodiments of the present invention, the sensor may be substantially isolated from energy emitted by the ancillary energy source when the energy treatment device is in sufficient contact with the surface to be treated.

As part of the method of reducing non desired energy leakage from an energy treatment device of the present invention, the energy source may be positioned within an inner portion of the energy treatment device, and the sensor may be positioned outside the inner portion of the energy treatment device and in optical contact with the energy source, in a manner to enable the detection of energy produced by the energy source. The sensor may be substantially isolated from energy produced by the energy source when the energy treatment device is in sufficient contact with the surface to be treated.

According to some embodiments of the present invention, the method of reducing energy leakage from an energy treatment device may include activating an ancillary energy source to produce energy from the ancillary energy source. The ancillary energy source may be activated to produce an energy output having predetermined characteristics. The sensor may be activated to detect energy associated with the ancillary energy source. The amount of energy associated with the ancillary energy source that may be detected by the sensor and may be further analyzed by the controller to determine, whether the amount of energy associated with the ancillary energy source detected by the sensor is within a predetermined range. If the amount of energy associated with the ancillary energy source detected by the sensor is outside the predetermined range, the sensor may generate a signal indicating sufficient contact or full-contact between the energy treatment device and a surface to be treated.

According to some embodiments of the method of the present invention a therapeutic energy source may be enabled upon receiving a signal from the sensor indicating sufficient contact between the energy treatment device and a surface to be treated. However, if the amount of energy associated with the ancillary energy source detected by the sensor is within a predetermined range the sensor may generate a failure signal. The failure signal may indicate insufficient contact between the energy treatment device and the surface to be treated.

According to some embodiments of the method of the present invention, the therapeutic energy source may be disabled upon receiving a signal from the sensor indicating no sufficient contact between the energy treatment device and the surface to be treated.

Some embodiments of the present invention may include enabling the therapeutic energy source upon the receipt of a signal from the sensor indicating sufficient contact between the energy treatment device and a surface to be treated from two or more sensors. Some embodiments of the present invention may include disabling the therapeutic energy source upon the receipt of a signal from at least one of the first and the second sensors indicating insufficient contact between the energy treatment device and a surface to be treated. Further embodiments of the method of the present invention may include generating a signal indicating insufficient contact between the energy treatment device and a surface to be treated as a default signal. The signal might be interrupted when sufficient contact is achieved.

Figure 6:
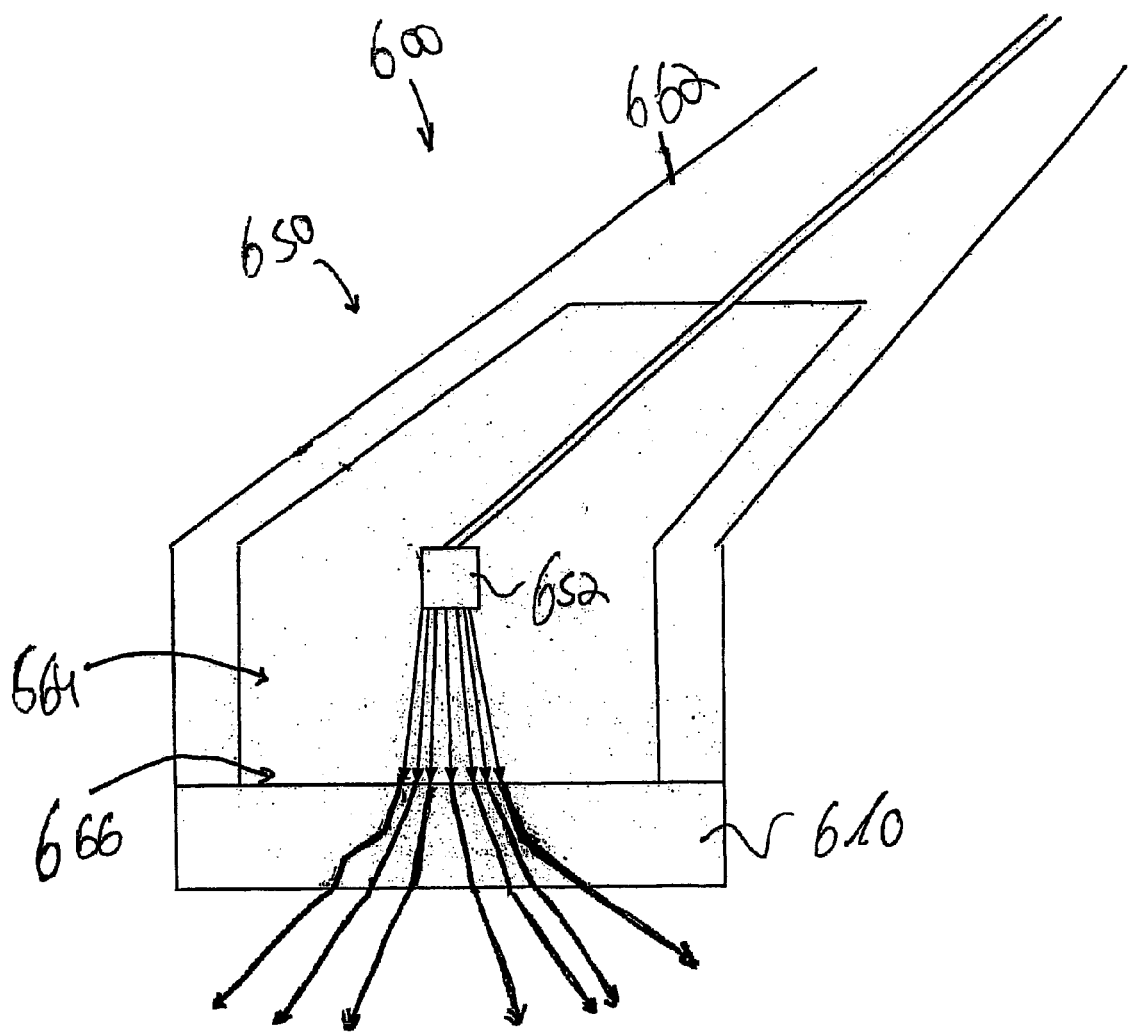
FIG. 6 is a block diagram illustration of an arrangement for reducing energy leakage from an energy treatment device in accordance with some embodiments of the present invention.

Reference is now made to FIG. 6, which is an illustration of an arrangement for preventing harmful effect resulted from energy leakage from an energy treatment device, in accordance with some embodiments of the present invention. As part of some embodiments of an arrangement for reducing energy leakage from an energy treatment device in accordance with the present invention, arrangement for reducing energy leakage from an energy treatment device may include a diffuser 610. The energy treatment device 600 may include a therapeutic energy source 652. The therapeutic energy source 652 may be adapted to produce therapeutic energy to be delivered to a surface to be treated. The diffuser 610 may be adapted to modify certain aspects, direction or parameters of the therapeutic energy. Once modified, the output therapeutic energy may be substantially harmless to tissue that is not the subject of treatment.

According to one embodiment of the present invention the diffuser 610 may include a milky glass block 610. The milky glass block may be adapted to scatter a collimated light passing through it. Those of ordinary skill in the art may appreciate that a diffused or a non-collimated laser beam is substantially less hazardous to such tissue and organs as the eyes than the same laser beam when collimated.

In the embodiment shown, the arrangement for preventing damage due to non-desired energy leakage from an energy treatment device is implemented in conjunction with a typical laser treatment device 600. The energy treatment device 600 may include accessory element in the form of a handpiece 650 and a therapeutic energy source 652. The therapeutic energy source may be also located elsewhere, with energy delivered via optic fiber to the treatment accessory 650. The accessory 650 may be a handpiece and may include a handle portion 662, an inner portion 664 and an output portion 666. The therapeutic laser source 652 may be positioned within the inner portion of the handpiece 664. The output portion 666 may include an aperture 672. The aperture 672 may allow the passage of energy from the therapeutic energy source 652 out of the handpiece 650. A milky glass block 610 may be fitted into the aperture 672. Accordingly, when the laser source 652 is activated the laser radiation may pass through the milky glass 610 where it may undergo a series of scatterings. This series of scattering may substantially diffuse the laser beam and may render the electromagnetic radiation substantially harmless to tissue that is not the target of the treatment. The diffuser 610 may also diffuse the energy delivered to the target, thus affecting lower tissue depths, but yielding higher safety.

As part of some embodiments of the present invention, two or more of the safety arrangements for promoting the safe operation of an energy treatment device by reducing energy leakage, may be implemented and cooperatively or alternatively operated in a single energy treatment device. In this case, there may be achieved a unified arrangement for promoting the safe operation of an energy treatment device that is substantially failsafe, wherein one such arrangement provides backup for the operation of the other such arrangements. Possibly, the input from the combined arrangements may be collected and processed conjointly. The collected and processed information from the combined arrangements may provide a more accurate and credible indication of energy leakage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What we claim is:

1. An arrangement for reducing energy leakage during an in vivo treatment from an energy treatment device comprising:
   at least one energy source configured to operate in a contact testing mode and in a therapeutic mode;
   at least one sensor to detect an energy signature associated with said at least one energy source; and
   a controller to enable a therapeutic mode of said energy source upon receiving a signal from said sensor indicating sufficient contact between the energy treatment device and a surface to be treated by the energy treatment device, such that a probability of energy leakage from said device during said treatment is reduced,
   wherein said energy source while operating in the contact testing mode is configured to produce energy that is insufficient to substantially affect a biological process when applied to a tissue.

2. The arrangement of claim 1, wherein said energy source while operating in the therapeutic mode is configured to produce energy that is sufficient to substantially affect a biological process when applied to a tissue.

3. An arrangement for reducing energy leakage during an in vivo treatment from an energy treatment device comprising:
   at least one energy source comprising at least one ancillary energy source and therapeutic energy source, wherein said ancillary energy source is configured to produce energy having predetermined characteristics;
   at least one sensor to detect an energy signature associated with said at least one energy source, said sensor configured to generate a signal when substantially no energy associated with said ancillary energy source is detected by said sensor; and
   a controller to enable a therapeutic mode of said energy source upon receiving said signal from said sensor indicating sufficient contact between the energy treatment device and a surface to be treated by the energy treatment device, such that a probability of energy leakage from said device during said treatment is reduced, wherein the energy produced by said ancillary energy is characterized in substantially poor penetration of the energy through superficial tissues.

4. An arrangement for reducing energy leakage during an in vivo treatment from an energy treatment device comprising:
   at least one energy source comprising at least one ancillary energy source and therapeutic energy source;
   at least one sensor to detect an energy signature associated with said at least one energy source;
   a controller to enable a therapeutic mode of said energy source upon receiving a signal from said sensor indicating sufficient contact between the energy treatment device and a surface to be treated by the energy treatment device, such that a probability of energy leakage from said device during said treatment is reduced; and
   a wave guide, wherein said ancillary energy source and said sensor are each coupled to said wave guide in a manner to enable the transmission of energy from said ancillary energy source to said sensor via said wave guide, wherein said wave guide is configured to provide efficient transmission of energy produced by said ancillary energy source when said wave guide is surrounded by air.

5. The arrangement of claim 4, wherein said wave guide is configured to enable the total internal reflection of energy produced by said ancillary energy source when said wave guide is surrounded by air.

6. The arrangement of claim 4, wherein said wave guide is configured to permit the leakage of a substantially predetermined amount of energy produced by said ancillary energy source when said wave guide is in a level of contact with skin tissue that is within a predetermined range.

7. The arrangement of claim 6, wherein said sensor is configured to generate a signal indicating sufficient contact between the energy treatment device and the surface to be treated when the amount of energy detected by said sensor is below a predetermined threshold.

8. The arrangement of claim 7, wherein said threshold is associated with said predetermined amount of energy leakage that is permitted when said wave guide is in sufficient contact with skin tissue.

9. An arrangement for reducing energy leakage during an in vivo treatment from an energy treatment device comprising:
   at least one energy source;
   at least one sensor to detect an energy signature associated with said at least one energy source;
   a variable transmission element having at least a first and second transmission modes; and
   a controller to enable a therapeutic mode of said energy source upon receiving a signal from said sensor indicating sufficient contact between the energy treatment device and a surface to be treated by the energy treatment device, such that a probability of energy leakage from said device during said treatment is reduced,
   wherein when said first mode of transmission of said variable transmission element is activated, said variable element is adapted to substantially block the passage of energy associated with said energy source through said variable transmission element.

10. The arrangement of claim 9, wherein when said variable transmission element is in said second mode of transmission, said variable element is adapted to permit the passage of energy associated with said energy source through said variable transmission element.

11. The arrangement of claim 10, wherein said second mode of transmission of said variable transmission element is activated upon receiving a signal from said sensor indicating insufficient contact between the energy treatment device and said surface to be treated by the energy treatment device.

12. The arrangement of claim 9, wherein said second mode of transmission of said variable element is activated upon receiving a signal from said sensor indicating sufficient contact between the energy treatment device and said surface to be treated by the energy treatment device.

* * * * *